(12) United States Patent
Hopkins et al.

(10) Patent No.: US 9,351,515 B2
(45) Date of Patent: May 31, 2016

(54) NUTRITIONAL COMPOSITION AND METHODS OF MAKING AND USING SAME

(75) Inventors: Anne Chace Hopkins, Diboll, TX (US); Matthew W. Lowe, Lufkin, TX (US)

(73) Assignee: Georgia-Pacific Panel Products LLC, Atlanta, GA (US)

( * ) Notice: Subject to any disclaimer, the term of this patent is extended or adjusted under 35 U.S.C. 154(b) by 402 days.

(21) Appl. No.: 13/514,885

(22) PCT Filed: Dec. 8, 2010

(86) PCT No.: PCT/US2010/059528
§ 371 (c)(1),
(2), (4) Date: Jun. 8, 2012

(87) PCT Pub. No.: WO2011/072051
PCT Pub. Date: Jun. 16, 2011

(65) Prior Publication Data
US 2013/0018015 A1   Jan. 17, 2013

Related U.S. Application Data

(60) Provisional application No. 61/267,570, filed on Dec. 8, 2009.

(51) Int. Cl.
| | | |
|---|---|---|
| *C08B 37/00* | (2006.01) | |
| *C08B 37/14* | (2006.01) | |
| *A23L 1/308* | (2006.01) | |
| *A61K 31/736* | (2006.01) | |
| *A23K 1/14* | (2006.01) | |
| *A23L 1/0534* | (2006.01) | |
| *A23L 1/30* | (2006.01) | |

(52) U.S. Cl.
CPC .............. *A23L 1/3082* (2013.01); *A23K 1/146* (2013.01); *A23L 1/0534* (2013.01); *A23L 1/3002* (2013.01); *A61K 31/736* (2013.01); *C08B 37/0087* (2013.01)

(58) Field of Classification Search
CPC .......................... C08B 37/0087; A61K 31/736
See application file for complete search history.

(56) References Cited

U.S. PATENT DOCUMENTS

| | | |
|---|---|---|
| 2,453,142 A | 11/1948 | Lee |
| 3,733,405 A | 5/1973 | Derrig |
| 3,796,797 A | 3/1974 | Parish et al. |
| 3,878,298 A | 4/1975 | Parish et al. |
| 3,988,483 A | 10/1976 | Deyoe et al. |
| 4,820,527 A | 4/1989 | Christensen et al. |
| 5,756,098 A | 5/1998 | Price et al. |
| 6,087,092 A * | 7/2000 | Richards ........................... 435/4 |
| 6,241,983 B1 | 6/2001 | Paul et al. |
| 6,783,780 B1 | 8/2004 | De Jong et al. |
| 7,048,937 B2 | 5/2006 | Dawson et al. |
| 7,109,005 B2 | 9/2006 | Eroma et al. |
| 7,291,607 B2 | 11/2007 | Day et al. |
| 7,625,728 B2 | 12/2009 | Eroma et al. |
| 7,638,151 B2 | 12/2009 | Duan et al. |
| 7,772,212 B2 | 8/2010 | Day et al. |
| 7,842,490 B2 | 11/2010 | Felby et al. |
| 7,993,689 B2 | 8/2011 | Duan et al. |
| 8,137,706 B2 | 3/2012 | Al-Ghazzewi et al. |
| 8,828,970 B2 | 9/2014 | Lowe et al. |
| 2003/0162300 A1 | 8/2003 | Kunz et al. |
| 2004/0091537 A1 | 5/2004 | Miller |
| 2004/0175460 A1 | 9/2004 | Zenovich |
| 2004/0176320 A1 | 9/2004 | Natunen et al. |
| 2005/0064447 A1 | 3/2005 | Huang |
| 2005/0079244 A1 | 4/2005 | Giffard et al. |
| 2005/0288250 A1 | 12/2005 | Rautonen et al. |
| 2006/0034978 A1 | 2/2006 | Deem et al. |
| 2006/0051812 A1 | 3/2006 | Helin et al. |
| 2006/0068022 A1 | 3/2006 | Playford |
| 2006/0182708 A1 | 8/2006 | Bockmuhl et al. |
| 2007/0141678 A1 | 6/2007 | Green et al. |
| 2007/0196890 A1 | 8/2007 | Vulevic et al. |
| 2007/0243268 A1 | 10/2007 | Jaffe |
| 2007/0298014 A1 | 12/2007 | Huang |
| 2009/0004327 A1 | 1/2009 | Duan et al. |
| 2009/0304852 A1 * | 12/2009 | Hopkins et al. .................. 426/2 |
| 2010/0028485 A1 | 2/2010 | Tuohy et al. |
| 2014/0378412 A1 | 12/2014 | Lowe et al. |

FOREIGN PATENT DOCUMENTS

| | | | |
|---|---|---|---|
| EP | 0143490 | A2 | 6/1985 |
| EP | 1407037 | B1 | 4/2004 |
| EP | 2025242 | A1 | 2/2009 |

(Continued)

OTHER PUBLICATIONS

De Castro, Fernando Basile, "The Use of Steam Treatment to Upgrade Lignocellulosic Materials for Animal Feed," Ph. D. Thesis, University of Aberdeen, Sep. 1994, 214 pages.
Office Action (Restriction Requirement) dated Apr. 8, 2013, 10 pages, U.S. Appl. No. 13/392,288, filed Feb. 24, 2012.
Office Action dated May 22, 2013, 24 pages, U.S. Appl. No. 13/392,288, filed Feb. 24, 2012.
Allision, Milton J., et al., "Synergistes jonesii, gen. nov., sp. nov.: A rumen bacterium that degrades toxic pyridinediols," System. Appl. Microbiol., 1992, pp. 522-529, vol. 15, Gustax Fischer Verlag, Stuttgart/ New York.
Azumi, H., et al., "Xylo-oligosaccharide composition is useful as medicine with high regulation effect of intestinal condition and is not decomposed by digestive fluids," XP-002656403 and JP 2001-226409 A, WPI Thomson, abstract, Aug. 21, 2001, 10 pages.

(Continued)

*Primary Examiner* — Eric Olson
(74) *Attorney, Agent, or Firm* — Ram W. Sabnis

(57) ABSTRACT

A Nutritional Composition comprising soluble extractable material from a lignocellulosic source. A method of producing a composition, comprising providing a lignocellulosic source, extracting soluble materials from the lignocellulosic source to produce soluble extractable material, and processing the soluble extractable material to yield a Nutritional Composition, wherein the Nutritional Composition comprises hemicellulose and exhibits pathogen blocking, anti-adhesion activity.

13 Claims, 3 Drawing Sheets

(56) References Cited

FOREIGN PATENT DOCUMENTS

| GB | 2404561 A | 2/2005 |
|---|---|---|
| JP | 2001226409 A | 8/2001 |
| JP | 2004229607 A | 8/2004 |
| JP | 2005027541 A | 2/2005 |
| JP | 4078778 B2 | 4/2008 |
| KR | 1019910004110 A | 3/1991 |
| KR | 100597659 B1 | 6/2006 |
| WO | 0033854 A1 | 6/2000 |
| WO | 03015533 A1 | 2/2003 |
| WO | 2004000340 A2 | 12/2003 |
| WO | 2005111195 A2 | 11/2005 |
| WO | 2005111195 A3 | 11/2005 |
| WO | 2007056432 A2 | 5/2007 |
| WO | 2007091231 A1 | 8/2007 |
| WO | 2009117790 A2 | 10/2009 |
| WO | 2009152089 A2 | 12/2009 |
| WO | 2009152089 A3 | 12/2009 |
| WO | 2010089453 A1 | 8/2010 |
| WO | 2011031531 A2 | 3/2011 |
| WO | 2011031531 A3 | 3/2011 |
| WO | 2011072051 A2 | 6/2011 |
| WO | 2011072051 A3 | 6/2011 |

OTHER PUBLICATIONS

Bar-Shavit, Zvi, et al., "Mannose-binding activity of *Escherichia coli*: a determinant of attachment and ingestion of the bacteria by macrophages," Aug. 1980, pp. 417-424, vol. 29, No. 2, Infection and Immunity.

Chaney, Albert L., et al., "Modified reagents for determination of urea and ammonia," 1962, pp. 130-132, vol. 8, No. 2, Clinical Chemistry.

Crawford, D. F., et al., "Evaluation of concentrated hemicellulose extract as cattle feed," XP-002580031, Journal of Animal Science, 1978, vol. 46, No. 1, pp. 32-40.

Ebringerová, Anna, et al., "Norway spruce galactoglucomannans exhibiting immunomodulating and radical-scavenging activities," International Journal of Biological Macromolecules, 2008, pp. 1-5, vol. 42, Elsevier B.V.

Foreign communication from a related counterpart application—International Search Report and Written Opinion, PCT/US2009/046605, Jan. 20, 2010, 7 pages.

Foreign communication from a related counterpart application—International Search Report and Written Opinion, PCT/US2010/046867, Jun. 1, 2011, 11 pages.

Foreign communication from a related counterpart application—Supplementary European Search Report, Application No. EP 09763380.4, Aug. 23, 2011, 11 pages.

Foreign communication from a related counterpart application—International Search Report and Written Opinion, PCT/US2010/059528, Aug. 30, 2011, 10 pages.

Foreign communication from a related counterpart application—International Preliminary Report on Patentability, PCT/US2010/046867, Feb. 28, 2012, 7 pages.

Gedek, B. R., "Adherence of *Escherichia coli* serogroup 0 157 and the Salmonella Typhimurium mutant DT 104 to the surface of *Saccharomyces boulardii*," Mycoses, 1999, pp. 261-264 plus 1 page publishing information, vol. 42, © 2002 EBSCO Publishing.

González-Muñoz, M. J., et al., "Production of hemicellulosic sugars from Pinus pinaster wood by sequential steps of aqueous extraction and acid hydrolysis," Wood Sci Technol, 2012, pp. 271-285, vol. 46, Springer-Verlag.

Jouany, Jean-Pierre, "Rumen microbial metabolism and ruminant digestion," 1991, pp. 217-237 plus 2 pages cover and publishing information, INRA Editions, Paris.

Mandre Malle, et al., "The quality of stemwood of Pinus sylvestris in an alkalised environment," Water Air Soil Pollut, 2007, pp. 163-172, vol. 182, Springer Science + Business Media B.V.

Mirelman, David, et al., "Screening of bacterial isolates for mannose-specific lectin activity by agglutination of yeasts," Apr. 1980, pp. 328-331, vol. 11, No. 4, Journal of Clinical Microbiology.

Moure, Andrés, et al., "Advances in the manufacture, purification and applications of xylo-oligosaccharides as food additives and nutraceuticals," XP-002656401, Process Biochemistry, 2006, vol. 41, pp. 1913-1923, Elsevier Ltd.

Nabarlatz, Debora Alcida, "Autohydrolysis of agricultural by-products for the production of xylo-oligosaccharides," Dissertation, Departament d'Enginyeria Quimica, Universitat Rovira I Virgili, Sep. 29, 2006, pp. 1-4, 19-22, and cover page, Tarragona.

Nacos, M. K., et al., "Kenaf xylan—a source of biologically active acidic oligosaccharides," Carbohydrate Polymers, 2006, vol. 66, issue 1, pp. 126-134, Elsevier Ltd.

Advisory Action dated Feb. 2, 2012 (3 pages), U.S. Appl. No. 12/480,171, filed Jun. 8, 2009.

Office Action dated Apr. 7, 2011 (18 pages), U.S. Appl. No. 12/480,171, filed Jun. 8, 2009.

Office Action (Final) dated Oct. 3, 2011 (11 pages), U.S. Appl. No. 12/480,171, filed Jun. 8, 2009.

Office Action dated Apr. 25, 2012 (12 pages), U.S. Appl. No. 12/480,171, filed Jun. 8, 2009.

Parajó, J.C., et al., "Production of xylooligo-saccharides by autohydrolysis of lignocellulosic materials," Trends in Food Science & Technology, 2004, vol. 15, pp. 115-120, Elsevier Ltd.

Pietarinen, Suvi, P., et al., "Knotwlle and bark extracts: strong antioxidants from waste materials," J Wood sci, 2006, pp. 436-444, vol. 52, The Japan Wood Research Society.

Provisional patent application entitled "Natural prebiotic derived from southern yellow pine polysaccharides," by Tom Lehtinen, et al., filed Dec. 9, 2008 as U.S. Appl. No. 61/121,005.

Provisional patent application entitled "Oligosaccharide prebiotic product processed from softwood molasses," by Tom Lehtinen, et al., filed Jun. 9, 2008 as U.S. Appl. No. 61/059,960.

Provisional patent application entitled "Ruminant gas reduction composition and methods of making and using the same," by Matthew W. Lowe, et al., filed Aug. 27, 2009 as U.S. Appl. No. 61/237,396.

Provisional patent application entitled "Nutritional composition and methods of making and using same," by Anne Chase Hopkins, et al., filed Dec. 8, 2009 as U.S. Appl. No. 61/267,570.

Salanitro, J. P., et al., "Quantitative method for the gas chromatographic analysis of short-chain monocarboxylic and dicarboxylic acids in fermentation media," Applied Microbiology, Mar. 1975, pp. 374-381, vol. 29, No. 3, American Society for Microbiology.

Vázquez, M.J., et al., "Enhancing the potential of oligosaccharides from corncob autohydrolysis as prebiotic food ingredients," Industrial Crops and Products, 2006, vol. 24, pp. 152-159, Elsevier, Ltd.

Vázquez, M.J., et al., "Enzymatic processing of crude xylo-oligomer solutions obtained by autohydrolysis of Eucalyptus wood," XP002656402, Food Biotechnology, abstract, 2002, 1 page.

Vázquez, M.J., et al., "Refining of autohydrolysis liquors for manufacturing xylo-oligosaccharides: evaluation of operational strategies," XP 025313229, Bioresource Technology, 2005, vol. 96, pp. 889-896, Elsevier, Ltd.

Vázquez, M. J., et al., "Xylooligosaccharides: manufacture and applications," Trends in Food Science & Technology, 2000, pp. 387-393, vol. 11, Elsevier Science Ltd.

Willför, Stefan, et al., "Spruce-derived mannans—A potential raw material for hydrocolloids and novel advanced natural materials," XP-002656400, Carbohydrate Polymers, 2008, pp. 197-210, vol. 72, Elsevier Ltd.

Foreign Communication from a related counterpart application—International Preliminary Report on Patentability, PCT/US2010/059528, Jun. 21, 2012, 8 pages.

Patent application entitled "Methods of making and using a ruminant gas reduction composition," by Matthew W. Lowe, et al., filed Feb. 24, 2012 as U.S. Appl. No. 13/392,288.

Foreign communication from a related counterpart application—European Examination Report, European Patent Application No. 09763380.4, May 23, 2012, 3 pages.

(56) References Cited

OTHER PUBLICATIONS

De Castro FB. The use of steam treatment to upgrade lignocellulosic materials for animal feed. Ph.D. Thesis, University of Aberdeen. Sep. 1994.

Filing receipt and specification for provisional patent application entitled "Oligosaccharide Prebiotic Product Processed from Softwood Molasses," by Tom Lehtinen, et al., filed Jun. 9, 2008 as U.S. Appl. No. 61/059,960.

Filing receipt and specification for provisional patent application entitled "Natural Prebiotic Derived from Southern Yellow Pine Polysaccharides," by Tom Lehtinen, et al., filed Dec. 9, 2008 as U.S. Appl. No. 61/121,005.

Filing receipt and specification for provisional patent application entitled "Ruminant Gas Reduction Composition and Methods of Making and Using the Same," by Matthew W. Lowe, et al., filed Aug. 27, 2009 as U.S. Appl. No. 61/237,396.

Filing receipt and specification for provisional patent application entitled "Nutritional Composition and Methods of Making and Using the Same," by Anne Chace Hopkins, et al., filed Dec. 8, 2009 as U.S. Appl. No. 61/267,570.

Foreign communication from a related counterpart application—United Kingdom Examination Report, Application No. GB1205330.2, May 1, 2013, 3 pages.

Kenealy, William, et al., "Vapor-phase diethyl oxalate pretreatment of wood chips: Part 2. Release of hemicellulosic carbohydrates," Holzforschung, 2007, pp. 230-235, vol. 61, Walter de Gruyter.

Office Action (Final) dated Oct. 3, 2013 (26 pages), U.S. Appl. No. 12/480,171, filed Jun. 8, 2009.

Office Action dated Jan. 14, 2015 (32 pages), U.S. Appl. No. 12/480,171, filed Jun. 8, 2009.

Kačuráková, M., et al., "FT-IR study of plant cell wall model compounds: pectic polysaccharides and hemicelluloses," Carbohydrate Polymers, 2000, pp. 195-203, vol. 43, Elsevier Science Ltd.

Office Action (Final) dated Sep. 30, 2015 (32 pages), U.S. Appl. No. 12/480,171, filed Jun. 8, 2009.

Office Action dated Oct. 16, 2015 (256 pages), U.S. Appl. No. 14/465,634, filed Aug. 21, 2014.

Notice of Allowance dated Dec. 17, 2015 (14 pages), U.S. Appl. No. 12/480,171, filed Jun. 8, 2009.

Corrected Notice of Allowability dated Feb. 4, 2016 (6 pages), U.S. Appl. No. 12/480,171, filed Jun. 8, 2009.

\* cited by examiner

Effect of 17.5 mg Nutritional Composition/ml of medium on quantitative (A) and qualitative (B) measures of adherence of a green fluorescence protein labeled *Salmonella Typhimurium* to a non-immortalized porcine derived jejunal cell line (IPEC J2). Asterisks denote significant reductions in adhesion of the porcine intestinal cells by treated *Salmonella*.

NUTRITIONAL COMPOSITION AND METHODS OF MAKING AND USING SAME

CROSS-REFERENCE TO RELATED APPLICATIONS

This application is a filing under 35 U.S.C. 371 of International Application No. PCT/US2010/059528 filed Dec. 8, 2010, entitled "Nutritional Composition and Methods of Making and Using Same," claiming priority of U.S. Provisional Patent Application No. 61/267,570 filed Dec. 8, 2009, which applications are incorporated by reference herein in their entirety.

BACKGROUND

Renewable biological source materials such as plants and wood comprise various biological polymers. For example, carbohydrates (or saccharides) are a major component of wood. Chemically, carbohydrates are simple organic compounds that are aldehydes or ketones with a plurality of hydroxyl groups, usually one on each carbon atom that is not part of the aldehyde or ketone functional group. Carbohydrates are comprised of repeating monomeric units termed monosaccharides which can link together to form polymers referred to as polysaccharides and oligosaccharides, which are present in hemicellulose recovered from renewable raw materials such as wood.

Carbohydrates play many different roles in biological systems. They not only supply energy and structural material to the host animal, but their unique chemical characteristics provide a wealth of other functions. Carbohydrates that resist digestion in the small intestine but are fermentable in the large intestine have been shown to have added health benefits.

Adhesion of pathogenic organisms to host tissues is required for the initiation of most infectious diseases. For many bacteria, this adhesion is mediated by lectins present on the surface of the infectious organism that binds to complementary carbohydrates on the surface of the host tissues. Carbohydrates which are recognized by the bacterial surface lectins can bind to the pathogen by occupying the receptor site. This prevents the pathogen from attaching to the gastrointestinal mucosal cells, thus preventing colonization of the intestinal epithelium. Antibiotics have long been used to help control pathogens, but the effects of these agents on beneficial bacteria, and the development of antibiotic resistance, has created a need to identify alternatives which can reduce the incidence of pathogenic infections.

SUMMARY

Disclosed herein is a Nutritional Composition comprising soluble extractable material from a lignocellulosic source wherein the soluble extractable material comprises a hemicellulose. In an embodiment, the soluble extractable material comprises galactoglucomannans, xylans, arabinoxylans, or combinations thereof. In another embodiment, the soluble extractable material comprises galactoglucomannans and the galactoglucomannans comprise glucose monosaccharide units, galactose monosaccharide units, and mannose monosaccharide units in a ratio of about 3 to about 1 to about 6. In an embodiment, the lignocellulosic source comprises the above- and below-ground portions of a plant wherein the above-ground portion of a plant exhibits cambial growth. In another embodiment, the lignocellulosic source comprises a member of the family Pinaceae, a member of the family Fagaceae, a member of the order Saxifragales, or combinations thereof. In yet another embodiment, the lignocellulosic source comprises a member of the genus *Pinus*. In an embodiment, a dietary fiber comprises the Nutritional Composition. In another embodiment, an admixture comprises the Nutritional Composition and one or more pharmaceutical carriers.

Also disclosed herein is a method comprising administering the Nutritional Composition to an organism for prophylactic treatment of a gastrointestinal ailment.

Also disclosed herein is a food product comprising the Nutritional Composition.

Also disclosed herein is an admixture of the Nutritional Composition with one or more feed products, feed liquids, feed supplements, or combinations thereof.

Also disclosed herein is a method of producing a composition, comprising providing a lignocellulosic source; extracting soluble materials from the lignocellulosic source to produce soluble extractable material; and processing the soluble extractable material to yield a Nutritional Composition, wherein the Nutritional Composition comprises hemicellulose and exhibits pathogen blocking activity. In an embodiment, extracting soluble materials comprises softening the lignocellulosic source. In an embodiment, softening of the lignocellulosic source comprises autohydrolysis, pulping, steam explosion, steam extrusion, or combinations thereof. In an embodiment, the hemicellulose comprises monomers, oligosaccharides, and polysaccharides having a degree of polymerization from 1 to greater than about 10,000. In an embodiment, the hemicellulose comprises monomers, oligosaccharides, and polysaccharides having a degree of polymerization from 1 to greater than about 1,000. In an embodiment, the hemicellulose comprises monomers, oligosaccharides, and polysaccharides having a degree of polymerization from 1 to greater than about 500. In an embodiment, the hemicellulose comprises galactoglucomannans; other oligosaccharides and polysaccharides consisting of galactose, glucose, xylose, and/or arabinose; polyphenolics, or derivatives thereof; or combinations thereof. In an embodiment, the soluble extractable materials comprise monosaccharides, oligosaccharides, and polysaccharides composed of glucose, galactose, and mannose units in a ratio of about 3 to about 1 to about 6. In an embodiment, the method further comprises hydrolyzing the soluble extractable materials to produce a hydrolyzed composition. In an embodiment, the hydrolyzed composition comprises polysaccharides having a degree of polymerization of from about 2 to about 20. In an embodiment, the method further comprises dehydrating the soluble extractable materials.

Also disclosed herein is a method comprising administering the Nutritional Composition to an organism having a gastrointestinal system. In an embodiment, administration of the Nutritional Composition improves the gastrointestinal health of the organism. In an embodiment, the administration of the Nutritional Composition results in the prevention and/or treatment of adhesion of pathogenic organisms to the intestinal wall. In an embodiment, administration of the Nutritional Composition improves production of an organism-derived commodity, a biological function, or combinations thereof. In an embodiment, the organism derived product or commodity comprises eggs, meat, milk, wool, or combinations thereof. In an embodiment, the biological function comprises nutrient uptake, muscle growth, muscle development, weight gain, coat growth, survival, or combinations thereof. In an embodiment, the Nutritional Composition is administered as a food-additive and/or feed-additive.

DETAILED DESCRIPTION

Figure 1:
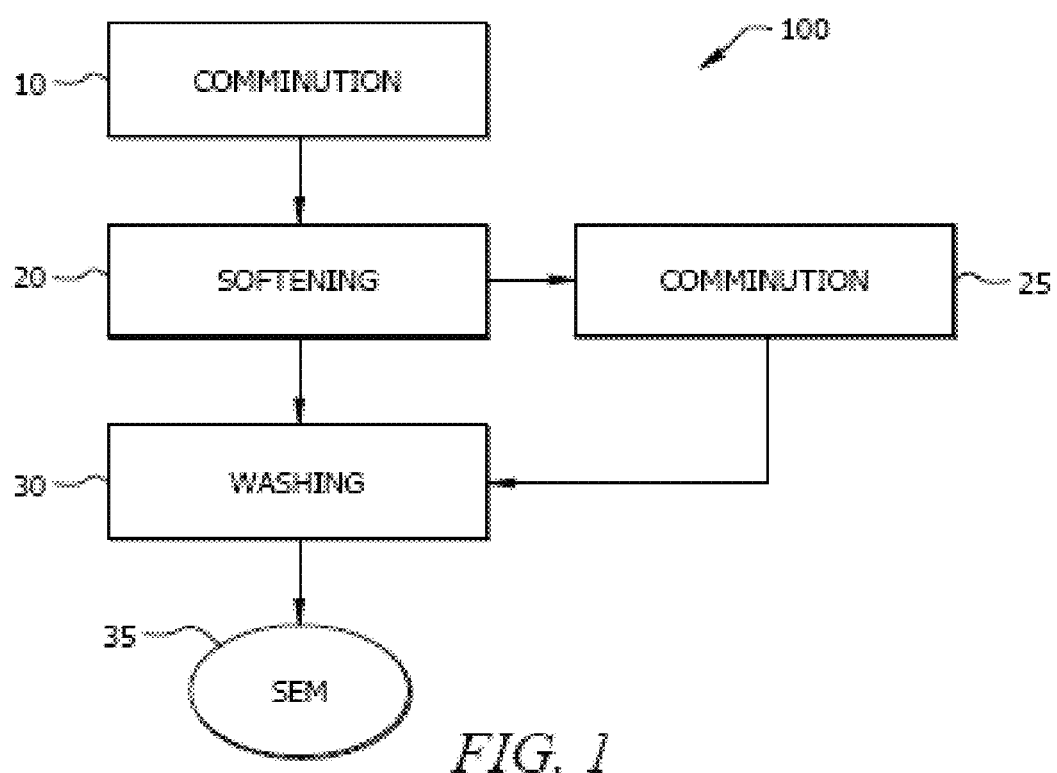
FIG. 1 is a flowchart of a method for isolating a pathogen blocking material.

Although an illustrative implementation of one or more embodiments may be provided below, the disclosed systems and/or methods may be implemented using any number of techniques. This disclosure should in no way be limited to the illustrative implementations, drawings, and techniques illustrated below, including the exemplary designs and implementations illustrated and described herein, but may be modified within the scope of the appended claims along with their full scope of equivalents.

Disclosed herein is a Nutritional Composition and methods of making and using same. In an embodiment, the Nutritional Composition comprises soluble extractable materials from a lignocellulosic source. In an embodiment, the Nutritional Composition is derived from a renewable, biological source material such as wood, bark, foliage, and roots. As is understood by those of skill in the art, wood refers to the organic material produced as secondary xylem in the stems of trees comprising various biological polymers including cellulose, hemicellulose, pectin, and polyphenolic compounds.

In an embodiment, the Nutritional Composition is a pathogen blocking material (PBM) exhibiting pathogen blocking activity (PBA) and is derived from a lignocellulosic source material. Herein, the PBM may function to disrupt adhesion of the pathogen to one or more receptors and thus may also be described as an anti-adhesion or anti-adhesive material. In an embodiment, the Nutritional Composition may function to reduce pathogen-to-receptor adherence in a range from about 1% to about 100%. In an embodiment, the Nutritional Composition may function to reduce pathogen-to-receptor adherence in a range from about 5% to about 95%. In an embodiment, the Nutritional Composition may function to reduce pathogen-to-receptor adherence in a range from about 5% to about 95%. In another embodiment, the Nutritional Composition may function to reduce pathogen-to-receptor adherence in a range from about 10% to about 80%. In another embodiment, the Nutritional Composition may function to reduce pathogen-to-receptor adherence in a range from about 20% to about 60%. In another embodiment, the Nutritional Composition may function to reduce pathogen-to-receptor adherence in a range from about 30% to about 40%.

The Nutritional Composition may also function as a pathogen binder. Herein, the term "derived" refers to isolation of the material from an organism where it is present natively such that the material is no longer in contact with all components of its native milieu. In an embodiment, the PBM is derived from the above-ground portion of a plant source material. Nonlimiting examples of such plant source materials include rice, rice hulls, soybeans, cotton, corn, barley, sorghum, sugar cane, bamboo, canola, sunflower, maize, sesame, rapeseed, coconut, rye, lucerne, lentil, peas, soya, beans, safflower, *Poa* spp., *Panicum* spp., algae and byproducts or derivatives of production and processing of the aforementioned source materials. In embodiments wherein the plant source material is a member of the family Poaceae or Gramineae, the PBM is not derived from the caryopsis.

In another embodiment, the Nutritional Composition exhibiting PBA is derived from a lignocellulosic source material that exhibits cambial growth. For example, the source material may comprise a plant that is a member of the family Pinaceae, the family Fagaceae, or the order Saxifragales. Alternatively, the source material is derived from a member of the family Pinaceae. The family Pinaceae comprises coniferous trees commonly known as the pine family.

In embodiments, the source material comprises a material derived from a member of the genus *Pinus*. The genus *Pinus* comprises coniferous trees commonly known as the pines. In embodiments, the source material comprises a material derived from a member of at least one species collectively referred to as the Southern Yellow Pines (SYP). In embodiments, the source material comprises a material derived from a member of the species *Pinus taeda* L, and its hybrids commonly referred to as Loblolly Pine. In alternative embodiments, the source material comprises a material derived from a member of the species *Pinus elliotii* Englem, and its hybrids commonly referred to as the Slash Pine. In alternative embodiments, the source material comprises a material derived from a member of the species *Pinus echinata* Mill, and its hybrids commonly referred to as Shortleaf Pine. In alternative embodiments, the source material comprises a material derived from a member of the species *Pinus palustris* Mill, and its hybrids commonly referred to as the Longleaf Pines. Southern Yellow Pines of the type disclosed herein are native to the Southeast United States and may typically be found along the coastal plain from eastern Texas to southeast Virginia extending into northern and central Florida. These Southern Yellow Pines are also globally cultivated and as such it is contemplated other regions may also provide a source of such pines. Typically Southern Yellow Pines are characterized as having a height of 30-35 m (100-115 ft) and a diameter of 0.7 m (28 in) and may grow to 47 m (154 ft) with a diameter of 1.2 m (47 in). Southern Yellow Pines may also be characterized by bark that is thick, reddish-brown, and scaly with leaves that are dark green, needle-like, and occur in bundles of up to three. The leaves are often twisted and have a length ranging from 20-45 cm (8-18 in).

In embodiments, a process of deriving a PBM from a source material (e.g., wood) comprises comminuting the source material, extracting soluble material from the source material, and concentrating the extracted solubles. In an embodiment, a process of deriving a Nutritional Composition from a source material (e.g., wood) comprises comminuting the wood, extracting oligosaccharides and polysaccharides (e.g., hemicellulose) from the source material via contact with a solvent (e.g., water), and concentrating the solvent extract. In an embodiment, a process 100 of deriving a PBM from a source material is shown in FIG. 1.

In an embodiment, the process 100 of deriving a PBM from a source material optionally comprises comminution of the source material at block 10 to reduce the physical size of the source material. For example, the wood source material may be chipped or comminuted prior to extracting the soluble material. As will be appreciated by those of skill in the art, comminuting the wood source material is an appropriate means of reducing the wood to a size that is both manageable and efficient for continued processing. Suitable machinery known to those of skill in the art may be employed to comminute the source material, non-limiting examples of which include tub grinders, wood chippers, chip-n-saws, and the like. Further, the comminuted wood may be screened to ensure that the material is uniformly or substantially uniformly sized. In the following embodiments, it is presumed that the wood source material has been comminuted prior to further processing. Though one or more of the following embodiments may describe the performance of processes with respect to comminuted wood, it is specifically contemplated that comminution is not necessarily a prerequisite to these processes.

In an embodiment, the process 100 of deriving a PBM from a source material (e.g., wood) comprises extracting the soluble material from the wood. Any method known to one of ordinary skill in the art and not deleterious to the Nutritional Composition may be employed to extract the soluble material from the wood. In an embodiment, the process of extracting the soluble material from the wood comprises softening the source material (e.g., wood) at block 20, optionally comminuting the softened wood at block 25, and contacting the softened wood with one or more solvents at block 30 into which the soluble material may partition. Herein, "softening" refers to processes which decrease the structural integrity of the exposed cell walls of the source material.

In an embodiment, the source material (e.g., wood) is softened at block 20 using any methodology known to one of ordinary skill in the art and compatible with the components of the Nutritional Composition. Nonlimiting examples of such methodologies include thermal, thermomechanical, thermochemical, mechanical, chemical, hydrothermal, acid hydrolysis, alkaline hydrolysis, organosolvent treatment, enzyme treatment, or combinations thereof. In an embodiment, the methodology comprises steam explosion and decompression wherein the source material is subjected to steam, pressure, and elevated temperature for some specified time period to soften and dissolve cell wall constituents.

In an embodiment, the source material is softened by a technique comprising autohydrolysis. As used herein, the term "autohydrolysis" refers to the process of subjecting the source material to a high temperature in the absence of chemicals but with moisture wherein organic acids are formed from functional groups such as acetyl groups liberated from the source material.

Specifically, the autohydrolysis process may comprise introducing the source material (e.g., comminuted wood) into a steam digester. In embodiments, the comminuted wood is steamed at a pressure ranging from 18-300 p.s.i., alternatively, from 50-250 p.s.i., alternatively, from 75-225 p.s.i. In embodiments, the comminuted wood will be allowed to remain in the steam digester for a period up to 10 minutes, alternatively, up to 15 minutes, alternatively, up to 20 minutes. In an embodiment, temperatures within the steam digester range from 212-420° F., alternatively, from 290-340° F., alternatively, from 295-335° F., alternatively, from 300-330° F. Not seeking to be bound by any particular theory, introduction into the steam digester softens the woods chips, thereby increasing the efficiency of later processing steps which seek to extract the soluble material.

In an embodiment, the source material is softened by a technique comprising pulping. Any pulping process known to one of ordinary skill in the art and not deleterious to the PBM may be employed to soften the source material. Examples of such processes are described in greater detail below.

In an embodiment, the source material (e.g., comminuted wood) is pulped using a mechanical pulping process. In these embodiments, the mechanical pulping process comprises separating the component wood fibers via the use of a plurality of grindstones, refining discs, knives, and like machinery known to those of skill in the art to mechanically disintegrate the comminuted wood, thereby reducing the comminuted wood to the fibrous components.

In an embodiment, the source material is pulped by subjecting the material to a pulping agent. In these embodiments, the pulping process comprises subjecting the comminuted wood to one or more chemicals and/or enzymes which will break down the lignin that holds the fibrous components together. Thus, as the lignin is degraded, the fibers of the wood are separated. Nonlimiting examples of chemical pulping processes include acid hydrolysis, alkaline hydrolysis, organosolvent treatment and the like.

In some embodiments, other methodologies for softening the source material may be employed. Such methodologies may employ a variety of reaction parameters such as temperature, pressure, pH, varying reaction times, and the like to extract the soluble material from the wood. For example, the source material may be softened by a steam extrusion process. Herein, steam extrusion refers to a process wherein the source material (e.g., comminuted wood) is pressed through a die where compressed gases (e.g., steam) are developed and then expanded (released).

Hereinafter, the source material whether subjected to a process of the type described herein (e.g., optional comminution followed by autohydrolysis or pulping) is termed the refined source material and for simplicity will hereinafter be referred to as the "refined wood." In an embodiment, refined wood is recovered from the process after block 25 of FIG. 1.

In some embodiments, the process 100 further comprises comminuting the refined wood at block 25. Communition and methods of carrying out same have been described previously herein and may likewise be used to reduce the size of the refined wood. The communited, refined wood may be passed from block 25 to block 30 for washing as described below.

Referring again to FIG. 1, the process 100 of deriving a PBM from a source material may further comprise washing the refined wood 30. The refined wood may be washed by contacting the material with a wash solution. The wash solution may comprise any material compatible with the components of the PBM. In an embodiment, the wash solution is an aqueous solution; alternatively, the wash solution is water or consists essentially of water. Contacting of the refined wood and wash solution may be carried out using any suitable technique such as, for example, by showering the refined wood with a wash solution. As the refined wood is contacted with the wash solution, the extractable compounds may be dissolved in, or otherwise portioned into, the wash solution which may then be collected. In an embodiment, the soluble material comprising oligosaccharides and polysaccharides (e.g., hemicellulose) present in the refined wood will be dissolved, suspended in, or otherwise partitioned into the wash solution.

In some embodiments, softening of the source material and extraction of the soluble material may be carried out concomitantly using a process such as solid-liquid countercurrent extraction. Herein, solid-liquid countercurrent extraction refers to a process wherein a solid phase material (e.g., comminuted wood) and a liquid phase material (e.g., hot water) are contacted to each other by causing them to flow countercurrently to each other to adsorb part of the components contained in the liquid phase to the solid phase and simultaneously extract part of the components adsorbed to the solid phase into the liquid phase.

The wash solution obtained by the processes described herein comprises soluble material extractable from a source material of the type described previously herein. Hereinafter, the wash solution obtained as described is termed the soluble extractable material (SEM), as recovered at block 35 of FIG. 1. In an embodiment, processes of the type described herein result in the extraction of greater than about 50% of the hemicellulose present in the source material, alternatively greater than about 60, 65, 70, 75, or 80% of the hemicellulose present in the source material.

In an embodiment, the SEM may be further processed by concentrating the solution to form a concentrated liquid. In embodiments, the SEM is concentrated to between 40 and 70% solids; alternatively to between 12% to 40% solids; alternatively to between 70% to 90% solids. The solids found in the SEM comprise approximately 93% carbohydrate and polyphenolic material, approximately 4% ash, and less than approximately 1% each of protein, fat, or crude fiber and exhibit PBA.

In an embodiment, the SEM is dehydrated to remove excess moisture. The SEM may be dehydrated using any suitable dehydration process as known to those of skill in the art and compatible with the needs of the process (e.g., spray drying, drum drying). In an embodiment, the SEM may be dehydrated to a moisture content of less than about 18%; alternatively less than about 10%; alternatively less than about 5%. In an embodiment, the SEM is concentrated and/or dehydrated to yield a solids powder.

The SEM prepared as described herein may comprise monosaccharides, oligosaccharides, and polysaccharides. The term oligosaccharide herein refers to a polymer comprising from about 2 to about 20 monosaccharide units while a polysaccharide herein refers to a polymer comprising greater than about 20 monosaccharide units. The number of monosaccharide units in a given oligosaccharide is termed the "degree of polymerization" (DP). For example, the SEM may comprise polysaccharides having a DP of greater than about 100; alternatively greater than about 150, 200, 250, 300, 350, 400, 450, or 500. In an embodiment, the SEM may comprise monomers, oligosaccharides, and polymers ranging from about 2 to about 500 DP as will be described in more detail later herein.

In embodiments, the SEM comprises one or more oligosaccharides and/or polysaccharides comprising a polysaccharide backbone; that is, the backbone comprises a plurality of glycosidically-linked monosaccharide units. In embodiments, the glycosidic linkage comprises a α-glycosidic link, a β-glycosidic link, or combinations thereof. In embodiments, the SEM comprises oligosaccharides comprising both α-glycosidic links and β-glycosidic links. In embodiments, the oligosaccharide will further comprise at least one side-chain. The side chain may comprise at least one monosaccharide unit glycosidically-linked to at least one saccharide unit of the polysaccharide backbone. Alternatively, the side chain may comprise at least one polysaccharide unit glycosidically-linked to at least one saccharide unit of the polysaccharide backbone.

In embodiments, the SEM comprises one or more oligosaccharides having monomeric units comprising an aldotriose monomer, an aldotetrose monomer, an aldopentose monomer, an aldohexose monomer, a ketotriose monomer, a ketotretrose monomer, a ketopentose monomer, a ketohexose monomer, a ribose monomer, an arabinose monomer, a xylose monomer, a lyxose monomer, an allose monomer, an altrose monomer, a glucose monomer, a mannose monomer, a gulose monomer, an idose monomer, a galactose monomer, a talose monomer, a ribulose monomer, a xylulose monomer, a psicose monomer, a fructose monomer, a sorbose monomer, a tagatose monomer, or combinations thereof.

In an embodiment, the SEM is further processed to reduce the DP of the constituent polymers. The DP of the SEM constituent polymers (e.g., polysaccharides) may be reduced by cleaving one or more of the glycosidic bonds between the monomer units of an oligosaccharide. Various methods can be used to cleave some of the glycosidic bonds between the monomer units while preserving the integrity of the sugar units. For example, the glycosidic bonds may be hydrolyzed. Hydrolysis of the glycosidic bonds can be achieved through any mechanism known to one of ordinary skill in the art and compatible with the needs of the process. For example, hydrolysis of the glycosidic bonds may be carried out employing chemical, enzymatic, thermal, or ultrasonic processes. Process variables such as reagent concentration, pH, temperature, time, and reactant can determine the degree of hydrolysis. Thus, one of ordinary skill in the art with the benefits of this disclosure may select hydrolysis reaction conditions suitable for the production of various polymer chain lengths.

In embodiments, the SEM or fractions thereof comprise an oligosaccharide comprising monomeric units having glucose monomers, galactose monomers, and mannose monomers in the form of a galactoglucomannan (GGM). In embodiments, the GGM comprises a backbone of β-1-4 linked mannose units with randomly spaced glucose units included and occasional α-1-6 galactose unit side chains. In embodiments, the hydroxyl groups of one or more monomeric units comprising the GGM backbone are partially substituted with O-acetyl groups at C-2 and C-3 positions. A non-limiting representative GGM structure is shown in Structure 1:

Structure 1

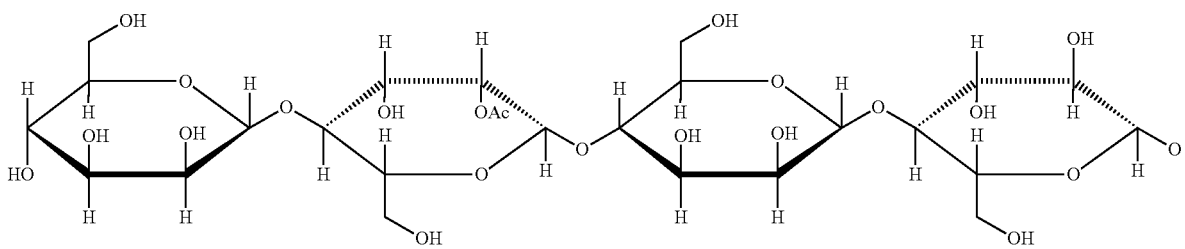

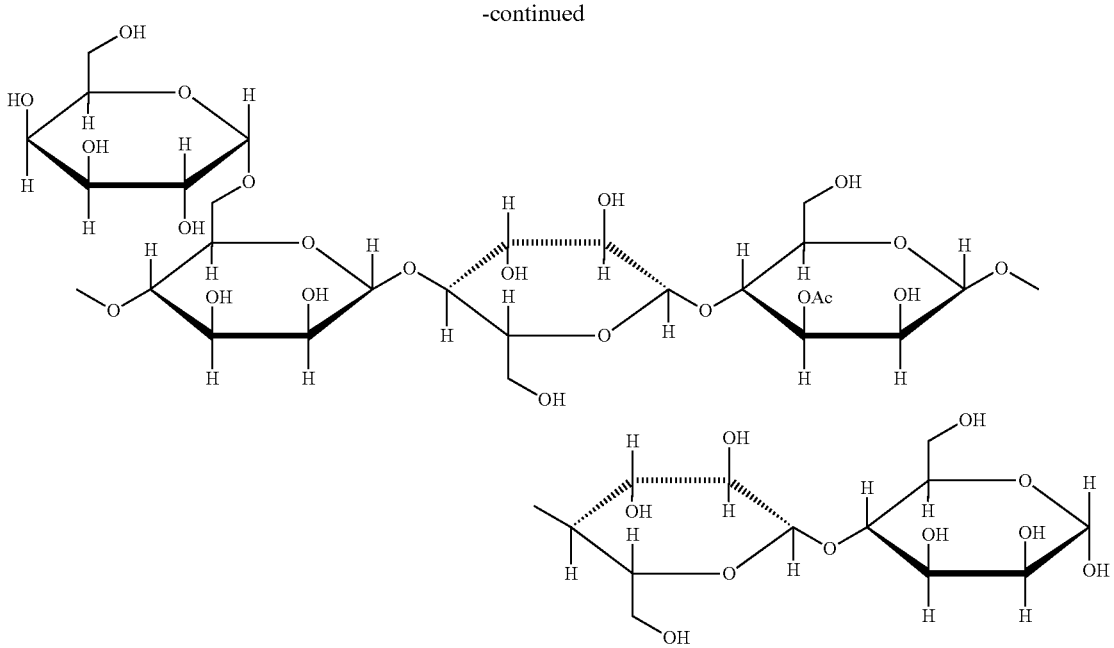

-continued

In an embodiment, the GGM oligosaccharide comprises glucose, galactose, and mannose in a ratio of 3 to 1 to 6 respectively.

For simplicity hereinafter the disclosure will refer to a Nutritional Composition It is to be understood said Nutritional Composition is obtained from a source material of the type described herein using the methodologies described herein. The Nutritional Composition may comprise the SEM components or fractions thereof (e.g., fractions having a given DP), derivatives thereof, or combinations thereof, of the type described herein.

In an embodiment, the Nutritional Composition comprises hemicelluloses comprising xylans, arabinoxylans, GGMs, or combinations thereof. In an embodiment, the Nutritional Composition comprises the SEM, SEM-derived fraction. In an embodiment, the Nutritional Composition comprises a GGM having a galactose:glucose:mannose ratio of about 3:1:6.

In an embodiment, the Nutritional Composition described herein displays PBA. Without wishing to be limited by theory, the PBA of the Nutritional Composition may be a result of the ability of the composition to function as an anti-adhesive agent. Particularly, the Nutritional Composition may reduce and/or eliminate the adhesion of pathogenic organisms to host tissue which is a common prerequisite for the initiation of infectious diseases. The Nutritional Composition described herein contains not only mannose, but also galactose, glucose, xylose, and/or arabinose, derivatives thereof, and polyphenolics all of which may offer anti-adhesion benefits. The anti-adhesive agents can be incorporated in the diet, thus offering a treatment or a prophylactic approach to control infections, thus improving the overall health of the animal.

In an embodiment, an effective amount of the Nutritional Composition may be administered to an organism and function as a PBM to confer beneficial health effects. Without wishing to be limited by theory, Nutritional Compositions of the type described herein may confer beneficial health effects by any number of mechanisms nonlimiting examples of which include competitive exclusion and/or pathogen binding and/or site colonization interference, production of short chain fatty acids and/or decrease in pH in the gastrointestinal (GI) tract of the organism to which it is introduced. In an embodiment, a Nutritional Composition of the type described herein may function as an anti-adherent that disrupts, reduces, and/or eliminates the adhesion of more than one type pathogen and/or disrupts, reduces, and/or eliminates the binding of a pathogen having more than one type of adhesion. Without wishing to be limited by theory, it is believed that some pathogens may display more than one type of adhesion, so that targeting only one out of several adhesions that the pathogens are capable of expressing may not be sufficient to prevent colonization and symptoms of infection. In an embodiment, pathogen binding is mediated by lectins present on the surface of the infectious organism that binds to a carbohydrate on the surface of the host tissue. For example, Type 1 fimbriae specifically bind to the glycoproteins that contain mannose on the intestinal cell surface. These are often referred to as mannose-binding lectins (MBL), and are known to bind to a wide range of intact microbes. Thus, a Nutritional Composition of the type described herein may offer demonstrable benefits of mannose binding lectins inhibition (e.g., anti-adhesion, anti-colonization, and pathogen-blocking), as well as activities (e.g., anti-adhesion, anti-colonization, and pathogen-blocking) associated with other saccharides, oligosaccharides, polysaccharides, polyphenolics, or combinations thereof that may be utilized (e.g., prevention of pathogen to host cell binding) advantageously in the prevention, amelioration, and/or treatment of disorders and/or dysfunctions associated with the infection of a host organism by pathogenic bacteria.

In an embodiment, a Nutritional Composition may be administered to an organism in order to confer beneficial health effects of the type described herein. Alternatively, the Nutritional Composition may be administered to an organism experiencing or anticipated to experience one or more adverse health events for which a PBM would ameliorate, mitigate, or prevent said adverse health event. For example, a Nutritional Composition may be administered to an organism experiencing an adverse health event involving the presence of pathogenic bacteria. Alternatively, a Nutritional Composition may be administered to an organism having an expectation of developing an adverse health event involving pathogenic bacteria. For example, an organism having been administered the pharmaceutical compositions may have an increased probability of one or more adverse events associated with the presence of pathogenic bacteria occurring. In an embodiment, an effective amount of a Nutritional Composition may be coadminstered with the pharmaceutical composition. Alternatively, an effective amount of a Nutritional Composition may be administered prior to and/or subsequent to administration of the pharmaceutical composition. In either embodiment, the administration of a Nutritional Composition may mitigate or prevent the development of adverse events associated with the use of the pharmaceutical composition.

In an embodiment, this disclosure provides for compositions comprising a Nutritional Composition and a pharmaceutically acceptable carrier. The term "composition" is intended to encompass a product comprising the active ingredient(s) (e.g., Nutritional Composition), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the compositions of the present disclosure encompass any composition made by admixing a Nutritional Composition, additional active ingredient(s), and pharmaceutically acceptable excipients.

The term "effective amount" as used herein means that amount of the Nutritional Composition that elicits the biological or medicinal response in a tissue, system, animal, or human that is being sought by a researcher, veterinarian, medical doctor, or other clinician. In one embodiment, the effective amount is a "therapeutically effective amount" for the alleviation of the symptoms of the disease, malady, condition, or combinations thereof being treated. In another embodiment, the effective amount is a "prophylactically effective amount" for prophylaxis of the symptoms of the disease, malady, condition, or combinations thereof, being prevented. It is contemplated that the compositions of the present disclosure may also be introduced to an organism in amounts less than a predetermined therapeutically and/or prophylatically effective amount. For example, a sub-effective amount of the disclosed compositions may be administered as an admixture of the composition with one or more food products and may serve to alter various properties of the food product (e.g., texture, appearance, taste, etc.).

To determine a Nutritional Composition dosing regime to provide an effective amount of the Nutritional Composition, accepted/customary methodologies and/or procedures for deriving the desired and/or effective amount of a Nutritional Composition to be provided to a subject organism may be employed. Non-limiting examples of such methodologies/procedures may comprise determining a relationship between a mass of the Nutritional Composition and a volume an organism's digestive system component, e.g., a concentration value for the Nutritional Composition; and determining a percent of an organism's total dietary mass consumption that is provided by the mass of the Nutritional Composition consumed by the organism, e.g., an inclusion rate for the Nutritional Composition in a diet of an organism.

In an embodiment, the Nutritional Composition's concentration value may be in the range of about 0.010 mg/ml to about 100.00 mg/ml. In embodiments, the Nutritional Composition's concentration value may be about 0.010 mg/ml, 0.015 mg/ml, 0.020 mg/ml, 0.025 mg/ml, 0.030 mg/ml, 0.035 mg/ml, 0.040 mg/ml, 0.045 mg/ml, 0.050 mg/ml, 0.055 mg/ml, 0.060 mg/ml, 0.065 mg/ml, 0.070 mg/ml, 0.075 mg/ml, 0.080 mg/ml, 0.085 g/ml, 0.090 mg/ml, or 0.095 mg/ml. In other embodiments, the Nutritional Composition's concentration value may be about 0.100 mg/ml, 0.125 mg/ml, 0.150 mg/ml, 0.170 mg/ml, 0.175 mg/ml, 0.180 mg/ml, 0.200 mg/ml, 0.500 mg/ml, 1.000 mg/ml, 1.500 mg/ml, 2.000 mg/ml, 2.250 mg/ml, 3.000 mg/ml, 3.350 mg/ml, 4.000 mg/ml, 4.500 mg/ml, 5.000 mg/ml, 5.500 mg/ml, 6.000 mg/ml, 6.650 mg/ml, 7.000 mg/ml, 7.500 mg/ml, 8.000 mg/ml, 8.500 g/ml, 9.000 mg/ml, or 9.950 mg/ml. In other embodiments, the Nutritional Composition's concentration value may be about 10.00 mg/ml, 15.00 mg/ml, 17.00 mg/ml, 17.50 mg/ml, 18.00 mg/ml, 20.00 mg/ml, 25.00 mg/ml, 30.00 mg/ml, 35.00 mg/ml, 40.00 mg/ml, 45.00 mg/ml, 50.00 mg/ml, 55.00 mg/ml, 60.00 mg/ml, 65.00 mg/ml, 70.00 mg/ml, 75.00 mg/ml, 80.00 mg/ml, 85.00 mg/ml, 90.00 mg/ml, 95.00 mg/ml, or 100.00 mg/ml. In all of the above-stated embodiments, the variance in the stated values may range from about 1% to 50%.

In an embodiment, the Nutritional Composition's inclusion rate (the percent of an organism's total dietary mass consumption that is provided by the mass of the Nutritional Composition consumed by the organism) may be in the range of about 0.01% to about 50%. In other embodiments, the Nutritional Composition's inclusion rate may be about 0.01%, 0.02%, 0.03%, 0.04%, 0.05%, 0.06%, 0.07%, 0.08%, 0.09%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, and 1.00%. In other embodiments, the Nutritional Composition's inclusion rate may be about 1.00%, 1.25%, 1.50%, 1.75%, 2.00%, 2.25%, 2.50%, 2.75%, 3.00%, 3.25%, 3.50%, 3.75%, 4.00%, 4.25%, 4.50%, 4.75%, and 5.00%. In other embodiments, the Nutritional Composition's inclusion rate may be about 5%, 6%, 7%, 8%, 9%, 10%, 15%, 20%, 25%, 30%, 35%, 40%, 45%, and 50%. In all of the above-stated embodiments, the variance in the stated values may range from about 1% to 50%.

Any suitable route of administration may be employed for providing an organism (e.g., human or animal) a Nutritional Composition. Dosage forms include tablets, troches, dispersions, suspensions, solutions, capsules, or combinations thereof, and the like. The most suitable route in any given case will depend on the nature and severity of the conditions being treated and on the nature of the active ingredient. They may be conveniently presented in unit dosage form and prepared by any of the methods well-known in the art of pharmacy.

In practical use, a Nutritional Composition can be combined as the active ingredient in intimate admixture with a pharmaceutical carrier according to conventional pharmaceutical compounding techniques. The carrier may take a wide variety of forms depending on the form of preparation desired for administration. In preparing the compositions for oral dosage form, any of the usual pharmaceutical media may be employed, such as, for example, water, glycols, oils, alcohols, flavoring agents, preservatives, coloring agents, and the like in the case of oral liquid preparations, such as, for example, suspensions, elixirs and solutions; or carriers such as starches, sugars, microcrystalline cellulose, diluents, granulating agents, lubricants, binders, disintegrating agents, and the like in the case of oral solid preparations such as, for example, powders, capsules, and tablets. Because of their ease of administration, tablets and capsules represent the most advantageous oral dosage unit form in which case solid pharmaceutical carriers may be employed. If desired, tablets may be coated by standard aqueous or nonaqueous techniques.

Pharmaceutical compositions comprising a Nutritional Composition suitable for oral administration may be presented as discrete units such as capsules, cachets, or tablets each containing a predetermined amount of the active ingredient (e.g., Nutritional Composition), as a powder or granules or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active, or dispersing agent. Molded tablets may be made by molding in a suitable machine, a mixture of the powdered compound moistened with an inert liquid diluent.

Nutritional Compositions may be used in combination with other drugs that are used in the treatment/prevention/suppression or amelioration of the adverse health events for which Nutritional Compositions of the type described herein are useful.

In an embodiment, the Nutritional Composition is administered to an organism having a GI tract. Administration of the Nutritional Composition may comprise preparing the Nutritional Composition in a suitable orally ingestible form and providing the suitable orally ingestible form to the organism. Suitable orally ingestible forms are discussed herein in further detail, although other suitable ingestible forms and methods of formulating same will be appreciable by those of skill in the art with the aid of this disclosure.

In an embodiment, a suitable orally ingestible form comprises a Nutritional Composition incorporated within a food, feed, or fodder product. The Nutritional Composition may be incorporated within the food, feed, or fodder product as a dry powder or a liquid. Nonlimiting examples of food, feed, or fodder products into which the Nutritional Composition may be incorporated include compound feeds and premixes such as pellets, nuts, nuggets, oil cakes, press cakes, various meals (e.g., fishmeal), or combinations thereof. Such food, feed, or fodder product may be prepared by admixing or blending the Nutritional Composition with a suitable carrier or diluent. Nonlimiting examples of suitable carriers may include grass and other forage plants, plant oils, seeds, grains, crop residues, sprouted grains, legumes, alfalfa meal, soybean meal, cottonseed oil meal, linseed oil meal, sodium chloride, cornmeal, molasses, urea, corncob meal, rice kernel, and the like. The carrier promotes a uniform distribution of the active ingredients in the finished feed into which the carrier is blended. It thus may ensure proper distribution of the active ingredient throughout the food, feed, or fodder product.

In an embodiment, a suitable orally ingestible form comprises a Nutritional Composition prepared as a nutritional supplement. Such a nutritional supplement may be ingestible by an organism alone or with another food, feed, fodder, forage product, snack, treat, or enjoyment product. In various embodiments, nutritional supplements may be prepared in a wet, semi-wet, or dry form. Nonlimiting examples of suitable nutritional supplement forms include powders, granules, syrups, and pills; other suitable forms will be known to those of skill in the art with the aid of this disclosure. In an embodiment, a nutritional supplement may be added to another food, feed, fodder, or forage product. For example the nutritional supplement may comprise a powder or syrup which is dispensed with (e.g., poured onto) hay, pellets, forage, or the like. Alternatively, in an embodiment, a nutritional supplement is provided without any other food or nutrient. For example, the nutritional supplement may comprise a syrup or gel which may be licked by an organism (e.g., from a tub or other suitable dispenser) or water-soluble powder dissolved in water provided for ingestion by the organism. Other suitable means of dispensing a nutritional supplement will be appreciated by those of skill in the art viewing this disclosure.

As will be appreciated by those of skill in the art, the ingestible forms may be formulated for ingestion by one or more organisms, nonlimiting examples of which include humans, livestock such as cattle, swine, horses, sheep, goats, poultry, fish, domesticated companionship species such as dogs, cats, fish, and rodents or undomesticated wildlife such as deer, moose, elk, migratory and non-migratory fowl, decapods, and fish.

In an embodiment, administration of a Nutritional Composition improves the overall health of the organism to which it is administered. In some embodiments, the overall improved health of the organism may be evidenced by an increase in biological functions such as nutrient uptake, muscle growth, muscle development, weight gain, coat growth, survival, or combinations thereof. In another embodiment, administration of the Nutritional Composition to an organism results in an increased yield in an organism derived commodity such as eggs, meat, milk, wool, or combinations thereof. In another embodiment, administration of the Nutritional Composition to an organism results in a decrease in the incidence and/or severity of disease.

EXAMPLES

The embodiments having been generally described, the following examples are given as particular embodiments of the disclosure and to demonstrate the practice and advantages thereof. It is to be understood that the examples are presented herein as a means of illustration and are not intended to limit the specification of the claims in any manner.

Example 1

To test the effects of a Nutritional Composition, of the type described herein, on mannose-specific binding activity of *Salmonella enterica serovar Typhimurium*, a qualitative agglutination test (Mirelman et al., 1980) was conducted except using *Saccharomyces boulardii* as the lectin-producing host (Gedek, 1999) as commercially acquired *Saccharomyces cerevisiae* cells did not support agglutination. Yeast cells grown in medium containing 1% yeast extract and 2% each of peptone and glucose (wt/vol) were harvested via centrifugation (15 min at 10,000×g). Cells were washed once with phosphate buffer (pH 7.4), pelleted again via centrifugation (15 min at 10,000×g) and resuspended in fresh phosphate buffer to a final concentration of approximately 0.1 g wet wt/ml. Bacterial cultures were grown overnight in tryptic soy broth (TSB) and harvested and washed as described above. Agglutination tests were performed by combining 50 µl of yeast suspension with 50 µl of bacterial suspension on a microscope slide. Upon exposure to the yeast cells, bacterial cells exhibiting profuse cell clumping within 3 minutes exposure were interpreted as a positive agglutination reaction. Each bacterial suspension was subsequently tested for specificity against mannose residues via pre-exposure of fresh bacterial cells to 50 μl 0.05 M methyl α-D-mannoside for approximately 2 to 3 minutes before reaction with the yeast cell suspension. The absence of agglutination was interpreted as a positive indication of mannose specificity. Tests for effect of the Nutritional Composition were conducted by pre-exposing fresh bacterial cells to 25 μl of 0.02, 0.04, or 0.07 g Nutritional Composition/ml as above and then combining with yeast cells suspensions. Reactions showing inhibition of agglutination were interpreted as the Nutritional Composition inhibiting bacterial binding to yeast cells.

Test strains of *Salmonella enterica* serovar *Typhimurium* exhibited mannose-specific lectin binding to *Saccharomyces boulardii* yeast cells (Table 1). A ruminal *Escherichia coli* isolated confirmed via PCR to be fimbrial negative was used as a negative control and as expected did not bind to and, thus, did not agglutinate with the yeast cells. Pre-exposure of the *Salmonella* strains to 25 μl bacterial cells to 0.04 and 0.07 g Nutritional Composition/ml prevented agglutination when mixed with yeast cells, providing evidence that the product inhibits binding of *Salmonella* to mannose-specific lectins expressed by *Saccharomyces boulardii* (Table 1).

TABLE 1

Effect of Nutritional Composition on mannose-specific lectin binding of *Salmonella enterica* to *Saccharomyces boulardii*

| Bacteria | Reaction | Effect of Nutritional Composition on agglutination reaction[a] | | |
|---|---|---|---|---|
| | | 1X level | 2X level | 4X level |
| *Salmonella Typhimurium* (poultry isolate) | Agglutination | Agglutination | Agglutination | No agglutination |
| *Salmonella Typhimurium* (swine isolate) | Agglutination | Agglutination | No agglutination | No agglutination |
| *Salmonella Typhimurium* DT104 | Agglutination | Agglutination | No agglutination | No agglutination |
| *Escherichia coli* RCA-1 (negative control) | No agglutination | No agglutination | No agglutination | No agglutination |

[a]Tests for effect of Nutritional Composition on *Salmonella* binding to mannose-specific lectins expressed by *Saccharomyces boulardii* were accomplished by pre-exposing bacterial cells suspension to 25 μl of 0.02, 0.04 or 0.07 g Nutritional Composition/ml.

Example 2

Chemical Composition of Oligosaccharide Composition, as Compared to Controls

In this example, two sets of experiments were performed on a Nutritional Composition derived from Southern Yellow Pine species via the processes described in one or more of the foregoing embodiments. The chemical characteristics of the Nutritional Composition, Nutritional Composition-derived material, and a control a material were investigated.

| No. | SAMPLE | SOURCE | PROCESSING |
|---|---|---|---|
| 1 | Soluble Extractable Materials (SEM) | Soluble Extractable Materials | As produced according to conditions mentioned herein |
| 2 | PP | SEM-HHM | Mild acid hydrolyzed SEM, partially purified with ethanol precipitation, dried |
| 3 | PP-DP fractions | Precipitate | Purified glucogalactomannose oligosaccharide fractions separated by size - large DP 9-14, medium DP 6-8, small DP 3-5 |
| 4 | scFOS | beet or cane sugar | Commercially available oligosaccharide - included in study as a control |
| 5 | YCW product | yeast | Relatively crude preparation from inactivated yeast cells - included as a mannan control |

The PP sample is an enriched SEM fraction prepared by mild acid hydrolysis with 0.2M TFA, ethanol precipitation, centrifugation, and lyophilization. The three PP-DP fractions used in the experiment were prepared by passing the PP material through a size exclusion column to attain varying degrees of polymerization: 3-5 DP, 6-8 DP, and 9-14 DP.

Figure 2:
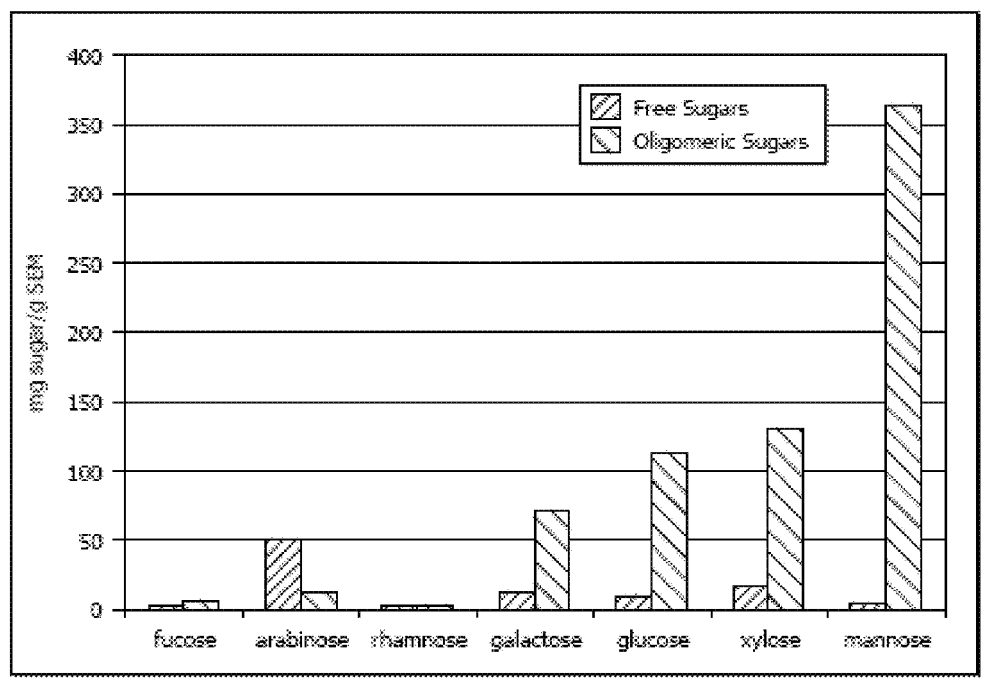
FIG. 2 is a graph illustrating total sugar composition for the samples from Example 1.

The scFOS sample is short chain fructooligosaccharide, a known, commercially available material. It is generally produced from sucrose by an enzymatic or fermentation process, and probably has a DP of 3-4. YCW product is an inactivated yeast product that is sold for use as a food additive with poultry, young livestock, and aquaculture feed and commercially available. In this example, the free sugars were first extracted from SEM-Sample 1 and analyzed using high pressure liquid chromatography (HPLC)/Ion Chromatography. Sample 1 was then subjected to complete depolymerization with sulfuric acid and the sugar content was again determined using HPLC/Ion Chromatography. The difference between the free sugars and the total sugars indicates the amount of oligomeric or polymeric sugars. FIG. 2 shows the amounts of free and oligomeric sugars present in the SEM, Sample 1, measured in mg of sugar per gram of Sample 1 (dry matter basis). This shows that galactose, glucose, xylose, and mannose are all present, mainly in oligomeric form. In these experiments, the compositional analysis of the samples tested indicated that all of the samples contained >90% organic matter, with the exception of the PP sample, Sample 3, which contained about 13% ash. This is likely due to the concentration of salts and ionic matter in the processing of SEM into PP.

Example 3

In this example, in vitro testing further demonstrated the ability of the Nutritional Composition to block mannose specific binding. Yeast cells and bacterial suspensions were prepared and agglutination tests were performed in a similar manner as indicated in Example 1. Results revealed that *Salmonella enterica* serovar *Typhimurium* labeled with a green fluorescent protein, as well as its genetic parent, exhibited mannose-specific binding. Two strains of *E. coli*, CVM 1569 and 1585 expressing F4 or F6 fimbriae, respectfully, also exhibited mannose specific lectin binding to *Saccharomyces boulardii* yeast cells. The agglutination activity for both suspensions of *Salmonella* and both suspensions of *E. coli* tested was inhibited when cells were treated with as little as 0.175 mg of Nutritional Composition/ml. The inhibition of agglutination indicates that the Nutritional Composition effectively inhibited bacterial binding to yeast cells.

Example 4

Figure 3:
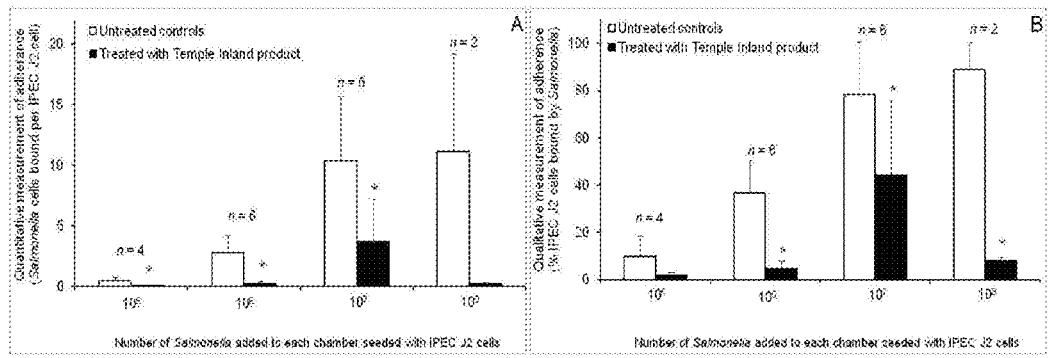
FIG. 3 is chart illustrating the qualitative and quantitative effects of the Nutritional Composition on the adherence of *Salmonella typhimurium* to a non-immortalized porcine derived jejunal cell line.

Many important enteric disease-causing organisms do not bind to the host epithelial tissue via mannose-specific fimbriae, but rather bind to other glyosyl receptors. This example demonstrates the ability of the Nutritional Composition, which also contains appreciable amounts of sugar moieties other than mannose, including galactose, glucose, xylose, and arabinose, as well as polyphenolics and other potentially bioactive compounds, to inhibit adherence of a non-mannose binding organism to porcine intestinal epithelial cells. Porcine derived IPEC J2 jejunal cells were seeded onto 8-well chamber slides. The cells used did not exhibit mannose sensitive adherence characteristics. The cells were exposed to suspensions containing a green fluorescent protein labeled *Salmonella enterica* serovar *Typhimurium* previously exposed for 10 minutes to an equal volume of water or to a suspension containing 17.5 mg Nutritional Composition/ml or 0.05M methyl α-D_mannoside. After the addition of treated or untreated bacteria, the chamber slides were incubated to allow attachment to occur and the wells of each slide were washed. Slides were examined by phase contrast microscopy at 1,000× magnification, and numbers of attached cells of the green fluorescent protein labeled *Salmonella enterica* serovar *Typhimurium* were counted on 100 randomly selected IPEC J2 cells. Pre-exposure of the green fluorescent protein-labeled *Salmonella Typhimurium* to 0.05M methyl α-D mannoside had no effect on *Salmonella* binding to the IPEC J2 cells, indicating that the adherence was via a mechanism independent of mannose-specific lectins. It was demonstrated that pre-exposure of the green fluorescent labeled *Salmonella Typhimurium* to 17.5 mg Nutritional Composition/ml significantly reduced ($P<0.05$) numbers of *Salmonella* observed to be bound to the IPEC J2 cells. The proportion of IPEC J2 cells bound by the *Salmonella* was also significantly reduced ($P<0.05$). See FIG. 3. These results demonstrate that the unique structure of the Nutritional Composition inhibits bacterial adherence via mechanisms including and additional to those mediated by Type 1 fimbriae.

Based on the in vitro effects of the Nutritional Composition on pathogen binding described in Examples 3 and 4, representative in vivo "Nutritional Composition effective amount" dosing regimes may be projected.

As shown in Example 3, 0.175 mg/ml of product demonstrated pathogen blocking effects. In an embodiment, an exemplary bovine species gut volume may be approximately 80,000 ml. Concomitantly, such an exemplary bovine may consume approximately 2.5-4.0% of its body weight per day. Thus, assuming said exemplary bovine weighs 1,200 lbs, the exemplary bovine's dietary intake would be approximately 30-48 lbs per day. Accordingly, given approximately 454,000 mg/lb, the Nutritional Composition dosing regime for said exemplary bovine could be calculated as: 30 lbs of intake—(0.175 mg/ml*80,000 ml)/(454,000 g/lb*30 lb)=0.001 or 0.1% of daily intake; and for 48 lbs of intake—(0.175 mg/ml*80,000 ml)/(454,000 mg/lb*48 lb)=0.0006 or 0.06% of daily intake. Thus, for said exemplary bovine, the dosing regime of the Nutritional Composition could be in the range from about 0.06% to about 0.1% of the exemplary bovine's daily dietary intake.

As shown in Example 4, 17.5 mg/ml of product demonstrated pathogen blocking effects. In an embodiment, another exemplary bovine species gut volume may be approximately 80,000 ml. Concomitantly, such an exemplary bovine may consume approximately 2.5-4.0% of its body weight per day. Thus, assuming said exemplary bovine weighs 1,200 lbs, the exemplary bovine's dietary intake would be approximately 30-48 lbs per day. Accordingly, given approximately 454,000 mg/lb, the Nutritional Composition dosing regime for said exemplary bovine could be calculated as: 30 lbs of intake—(17.5 mg/ml*80,000 ml)/(454,000 mg/lb*30 lb)=0.1028 or about 10% of daily intake; and for 48 lbs of intake—(17.5 mg/ml*80,000 ml)/(454,000 mg/lb*48 lb)=0.0642 or about 6% of daily intake. Thus, for said exemplary bovine, the dosing regime of the Nutritional Composition could be in the range from about 6% to about 10% of the exemplary bovine's daily dietary intake. Because organisms' digestive volumes, body masses, and daily dietary intake amounts can differ greatly, the actual Nutritional Composition dosing regime for a given organism could range from about 0.01% to about 50% of the daily dietary intake (by weight on a dry-weight basis).

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present invention. The discussion of a reference in the disclosure is not an admission that it is prior art, especially any reference that has a publication date after the priority date of this application. The disclosure of all patents, patent applications, and publications cited in the disclosure are hereby incorporated by reference, to the extent that they provide exemplary, procedural, or other details supplementary to the disclosure.

Reference is further made to the following specific embodiments:

1. A Nutritional Composition comprising soluble extractable material from a lignocellulosic source, wherein the Nutritional Composition exhibits one or more indications selected from the group consisting of pathogen blocking, anti-adhesion, pathogenic agglutination prevention, competitive exclusion, colonization interference, short chain fatty acid production, gastrointestinal tract pH reduction, pathogen-to-carbohydrate binding, and pathogen-to-glycoprotein binding.

The invention claimed is:

1. A method comprising:
   selecting an inclusion rate at which a Nutritional Composition will be included within the diet of an organism having a gastrointestinal system, wherein the inclusion rate is determined as a percent of an organism's total dietary mass consumption, wherein the inclusion rate is from about 0.01% to 50% of the organism's daily dietary intake; and
   administering, via dietary intake, the Nutritional Composition at the selected inclusion rate in an orally-administrable form including a powder, a capsule, a tablet, a pellet, a nut, a nugget, an oil cake, a press cake, or a meal formulation to the organism,
   wherein the Nutritional Composition comprises a soluble extractable material from a lignocellulosic source,
   wherein the soluble extractable material comprises galactoglucomannans having glucose units, galactose units, and mannose units in a ratio of about 3 to about 1 to about 6, and
   wherein the Nutritional Composition exhibits one or more indications selected from the group consisting of pathogen blocking, anti-adhesion, pathogenic agglutination prevention, competitive exclusion, colonization interference, short chain fatty acid production, gastrointestinal tract pH reduction, pathogen-to-carbohydrate binding, and pathogen-to-glycoprotein binding.

2. The method of claim 1, wherein the lignocellulosic source comprises a member of the family Pinaceae, a member of the family Fagaceae, a member of the order Saxifragales, or combinations thereof.

3. The method of claim 2, wherein the lignocellulosic source comprises a member of the genus *Pinus*.

4. The method of claim 1, wherein the Nutritional Composition exhibits the pathogen blocking indication.

5. The method of claim 1, wherein the Nutritional Composition exhibits the anti-adhesion indication.

6. The method of claim 1, wherein the Nutritional Composition exhibits the pathogenic agglutination prevention indication.

7. The method of claim 1, wherein the Nutritional Composition exhibits the competitive exclusion indication.

8. The method of claim 1, wherein the Nutritional Composition exhibits the colonization interference indication.

9. The method of claim 1, wherein the Nutritional Composition exhibits the short chain fatty acid production indication.

10. The method of claim 1, wherein the Nutritional Composition exhibits the gastrointestinal tract pH reduction indication.

11. The method of claim 1, wherein the Nutritional Composition exhibits the pathogen-to-carbohydrate binding indication.

12. The method of claim 1, wherein the Nutritional Composition exhibits the pathogen-to-glycoprotein binding indication.

13. The method of 1, wherein administering the Nutritional Composition reduces pathogen-to-receptor adherence in the organism's gastrointestinal system from about 1% to about 100%.

* * * * *

UNITED STATES PATENT AND TRADEMARK OFFICE
CERTIFICATE OF CORRECTION

PATENT NO. : 9,351,515 B2  
APPLICATION NO. : 13/514885  
DATED : May 31, 2016  
INVENTOR(S) : Anne Chace Hopkins et al.

Page 1 of 1

It is certified that error appears in the above-identified patent and that said Letters Patent is hereby corrected as shown below:

In the claims:

Claim 13, column 20, line 35, replace "The method of 1," with --The method of claim 1,--

Signed and Sealed this
Nineteenth Day of July, 2016

Michelle K. Lee
*Director of the United States Patent and Trademark Office*